United States Patent [19]

Pestronk

[11] Patent Number: 6,077,681
[45] Date of Patent: Jun. 20, 2000

[54] DIAGNOSIS OF MOTOR NEUROPATHY BY DETECTION OF ANTIBODIES

[75] Inventor: Alan Pestronk, St. Louis, Mo.

[73] Assignee: Washington University, St. Louis, Mo.

[21] Appl. No.: 08/885,977

[22] Filed: Jun. 30, 1997

[51] Int. Cl.$^7$ .................................................. G01N 33/53
[52] U.S. Cl. .................. 435/7.92; 435/7.95; 435/967; 435/975; 436/518; 436/524; 436/528; 436/532; 436/71; 436/811
[58] Field of Search ..................................... 435/7.1, 7.92, 435/7.94, 7.95, 967, 975; 436/506, 513, 518, 524, 528, 529, 530, 531, 532, 534, 63, 811, 71

[56] References Cited

PUBLICATIONS

Harlow et al, Antibodies a Laboratory Manual., Cold Spring Harbor Laboratory, 1988 pg. vi.

Roses et al eds, Manual of Clinical Laboratory Immunology, Third Edition, American Society for Microbiology, Washington D.C., 1986. pg. 88–98 and 101–102.

Taki et al. J. Biochem. 107: 493–498, 1990.

van Schalk et al., Neurology, 45: 1570–1577, 1995.

Ravindranath et al, Journal of Immunological Methods, 169:257–272, 1994.

Younes—Chennoufi et al., Neurochem. Int, 20(3):353–357, 1992.

*Primary Examiner*—Patricia A. Duffy
*Attorney, Agent, or Firm*—Hamilton, Brook, Smith & Reynolds, P.C.

[57] ABSTRACT

Methods of detecting antibody to GM1 ganglioside in a sample, comprising covalent linkage of GM1 ganglioside to a solid-phase reactant, are disclosed. The methods of detecting antibody to GM1 ganglioside can be used in methods of diagnosing motor neuropathies, such as multifocal motor neuropathy or immune-mediated motor neuropathy, in an individual. The amount of antibody specific to GM1 ganglioside in a test sample from a individual is measured; a titer of antibody to GM1 ganglioside that is greater than 1,800 is indicative of disease.

31 Claims, No Drawings

DIAGNOSIS OF MOTOR NEUROPATHY BY DETECTION OF ANTIBODIES

BACKGROUND OF THE INVENTION

Multifocal motor neuropathy (MMN) is a slowly progressive disorder of peripheral nerves that is characterized clinically by asymmetric, progressive, predominantly distal weakness in the upper extremities (Pestronk, A. et al., 1988, *Ann. Neurol.* 24:73–38; Kornberg, A. J. and Pestronk, A., 1995, *Ann. Neurol.* 37:S43–S50; Parry, G. J., "Motor neuropathy with multifocal conduction block", pp. 1518–1524 in *Peripheral Neuropathy* (Dyck, P. J. and Thomas, P. K., eds.), 3rd ed., W. B. Saunders, Philadelphia, 1993). Arms are involved more frequently than legs, and there is generally no bulbar, upper motor neuron, or sensory involvement (Bird, 1990, *Current Opinion Neurol. Neurosurg.* 3:704–707). Electrodiagnostic studies show focal blockage of impulse conduction along motor axons (Pestronk, A. et al., 1988, *Ann. Neurol.* 24:73–38; Parry, G. J., "Motor neuropathy with multifocal conduction block", pp. 1518–1524 in *Peripheral Neuropathy* (Dyck, P. J. and Thomas, P. K., eds.), 3rd ed., W. B. Saunders, Philadelphia, 1993). In more than eighty percent of patients, weakness begins in the hands and may progress slowly for periods up to twenty years. MMN is more common in males than females (2:1) and frequently (66 percent) begins in patients younger than 45 years of age.

Previous studies have shown that serum IgM antibodies to GM1 ganglioside are common in MMN, having been reported in 30% to 63% of patients (Kornberg, A. J. and Pestronk, A., 1995, *Ann. Neurol.* 37:S43–S50; Kornberg, A. J. and Pestronk, A., 1994, *Muscle Nerve* 17:100–104; Sadiq, S. A. et al., 1990, *Neurology* 40:1067–1072; Adams, D. et al., 1991, *Neuroimmunology* 32:223–230; Taylor, B. V. et al., 1996, *Neurology* 46:951–955). The target of serum antibodies, if any, in the remaining patients has been unclear. It has recently been found that IgM in patient sera binds to GM1 ganglioside as a component in a lipid mixture, GGC (GM1 ganglioside, galactocerebroside, and cholesterol sulfate) more commonly than to GM1 ganglioside alone (Pestronk, A. et al. (1997), *Neurology* 48:1104–1106). Enzyme-linked immunosorbent assays (ELISA) have been used for identification of antibodies to GM1 ganglioside (see, for example, Pestronk, A. et al. (1990), *Ann. Neurol.* 27:316–326; U.S. Pat. No. 5,443,952; and U.S. patent application Ser. Nos. 08/137,895, 08/481,144 and 08/789,86; the entire teachings of this reference, patent and patent applications are incorporated herein by reference in their entirety).

Electrophysiological testing in search of motor conduction block during the workup of MMN can be time consuming and, in some cases with severely affected nerves or equivocal findings, difficult to interpret. In addition, some immune-mediated motor neuropathies may not have conduction block. In these motor neuropathies antibody testing may be the only objective method of distinguishing the neuropathy from other motor neuron disorders such as amyotrophic lateral sclerosis (ALS). It is important to clarify the diagnosis, as immune disorders are often treated with modalities that are very expensive or associated with significant side effects. Methods of diagnosing motor neuropathies based on specific disease-related criteria would facilitate identification of treatable disease, reduce the time and expense associated with electrophysiological testing, and expedite commencement of treatment.

SUMMARY OF THE INVENTION

The present invention pertains to methods of determining, in a test sample, the amount of antibodies directed against a specific nervous system antigen, GM1 ganglioside, by using a modified solid-phase reactant. The method utilizes a solid-phase reactant, such as a microtiter plate, that is modified to allow covalent linkage of compounds on its surface. In one embodiment, the solid-phase reactant is modified to include secondary amino groups on its surface. The modified solid-phase reactant, referred to herein as a "covalent-linkage solid-phase reactant", is coated with GM1 ganglioside. One or more control antigens, such as other glycolipids, glycoproteins or carbohydrates, can also be coated on its surface. The covalent-linkage solid-phase reactant having GM1 ganglioside coated thereon is contacted with a test sample of a bodily fluid, such as a blood, serum, cerebrospinal fluid, or urine, from an individual. The level of antibodies in the test sample to GM1 ganglioside is then determined using standard methods, such as enzyme-linked immunosorbent assay (ELISA) or another appropriate solid-phase assay. If a control antigen is coated on the covalent-linkage solid-phase reactant, the level of antibodies in the test sample to the control antigen, can also be determined using the same methods specific reactivity to GM1 ganglioside is binding above levels of biding to the control antigen.

These methods of determining the amount of antibodies to GM1 ganglioside can be used for diagnosing motor neuropathies, such as multifocal motor neuropathy or immune-mediated motor neuropathy: a high titer of antibodies (for example, greater than about 1,800) is indicative of disease. The invention also pertains to test kits, containing modified solid-phase reactants, for use in the methods of the invention.

The methods of the invention detect antibodies to GM1 ganglioside in a significantly larger number of motor neuropathy patients; furthermore, increased titers of autoantibodies are also detected. The high sensitivity and specificity of the assays described herein can clarify the differential diagnosis of motor neuropathies and reduce the need for time-consuming and expensive electrophysiological evaluation.

DETAILED DESCRIPTION OF THE INVENTION

The invention described herein relates to methods of determining the amount of antibodies to GM1 ganglioside in a sample, and methods of diagnosing motor neuropathies, such as multifocal motor neuropathy or immune-mediated motor neuropathy, in an individual by determining the amount of antibodies to GM1 ganglioside in a sample from the individual. Applicant has discovered that high titer, selective IgM binding to GM1 ganglioside can be detected by conducting an enzyme-linked immunosorbent assay (ELISA) using microtiter plates that allow covalent attachment of glycolipids to the plates. Using plates modified by the addition of amino groups to allow covalent linkage of GM1 ganglioside, high titer (e.g., >1,800), selective serum IgM binding to GM1 ganglioside was detected in 85% (23 of 27) MMN patients. Titers of IgM anti-GM1 ganglioside antibodies, averaging 30,815±14,728 were more than four-fold higher ($p<0.001$) than found by using conventional plates (7,152±4,425) or using detection of GM1 ganglioside antigen in a lipid environment (3,567±1,338). This detection of serum IgM binding was significantly ($p<0.001$) greater than the level of IgM binding found using other testing methodologies, and showed disease specificity. Further, it was found that 33% (9 of 27) of MMN patient serums were negative using other assay methodologies tested, but had high titers of selective IgM binding to GM1 ganglioside when tested using the amino-containing plates. This frequency of occurrence of selective serum IgM antibodies to GM1 ganglioside, at titers with specificity for the disease, is much higher than the prevalence ranging from 30% to 63% found previously (Sadiq, S. A. et al., 1990, *Neurology* 40:1067–1072; Adams, D. et al., 1991, *Neuroimmunology* 32:223–230; Taylor, B. V. et al., 1996, *Neurology* 47:951–955). In addition, Chinese patients with acute immune neuropathies had high titers (>2,100) of selective IgM binding to GM1 ganglioside.

As a result of this discovery, highly sensitive and specific methods of determining the presence or absence, and the amount, of antibody to GM1 ganglioside in a sample are now available. In the methods, a modified solid-phase reactant is used. The term, "solid-phase reactant", as used herein, refers to a solid medium, such as a microtiter plate, a membrane (e.g., nitrocellulose), a bead, a dipstick, a thin-layer chromatographic plate, or other solid medium. In a preferred embodiment, the solid-phase reactant is a microtiter plate that can be used in a solid-phase immunoassay, such as an enzyme-linked immunosorbent assay. The solid-phase reactant is modified such that antigens, such as glycolipids, glycoproteins or carbohydrates, can be covalently linked on its surface. A representative solid-phase reactant that allows covalent linkage of antigens on its surface is a solid-phase reactant that has secondary amino groups thereon, such as the Nunc CovaLink NH microwell plate (Nunc; Roskilde, Denmark). A solid-phase reactant that has the ability to allow covalent linkage of antigens onto its surface is referred to herein as a "covalent-linkage solid-phase reactant".

GM1 ganglioside is adsorbed (coated) onto the covalent-linkage solid-phase reactant. A representative method of coating uses GM1 ganglioside dissolved in 1% N-(3-dimethylaminopropyl)-N-ethyl-carbodiimide (EDC). The GM1 ganglioside, dissolved in EDC, is incubated with the covalent-linkage solid-phase reactant. If the covalent-linkage solid-phase reactant contains secondary amino groups, it is believed that GM1 ganglioside, when exposed to the secondary amino groups, covalently links to the secondary amino groups. A covalent-linkage solid-phase reactant on which GM1 ganglioside is adsorbed is referred to herein as a "GM1-coated, covalent-linkage solid-phase reactant".

A control antigen, such as another glycolipid (e.g., GD1a ganglioside), or a glycoprotein or carbohydrates, can also be adsorbed onto the covalent-linkage solid-phase reactant. More than one control antigen can be used. The control antigen(s) can be coated onto the covalent-linkage solid-phase reactant using methods similar to those used to coat GM1 ganglioside onto the covalent-linkage solid-phase reactant. The control antigen is usually adsorbed on the covalent-linkage solid-phase reactant at a different location than the GM1 ganglioside. For example, if the solid-phase reactant is a microtiter plate, GM1 ganglioside can be coated onto certain wells of the plate, and the control antigen can be coated onto other wells of the plate. Alternatively, the control antigen can be adsorbed onto a separate solid-phase reactant, the separate solid-phase reactant being the same type of solid-phase reactant as that onto which the GM1 ganglioside is coated. It is intended that the term, "GM1-coated, covalent-linkage solid-phase reactant", refers to those covalent-linkage solid-phase reactants having GM1 ganglioside alone adsorbed thereon, and also to those covalent-linkage solid-phase reactants having GM1 ganglioside thereon and one or more control antigens adsorbed at a different location thereon. The term, "control antigen-coated covalent-linkage solid-phase reactant is used to refer to a solid-phase reactant having soley control antigen(s) coated thereon.

The GM1-coated, covalent-linkage solid-phase reactant (and control antigen-coated, covalent-linkage solid-phase reactant, if used) is used in an assay to determine the amount of antibody to GM1 ganglioside in a test sample. The test sample to be assayed for the amount of antibody to GM1 ganglioside can be a sample of bodily fluid or tissue from an individual For example, the test sample can comprise blood, serum, cerebrospinal fluid, urine, nasal secretion, saliva, or any other bodily fluid or tissue. Alternatively, the test sample can comprise antibodies, and particularly IgM, IgG and/or IgA antibodies, that have been isolated from a sample of bodily fluid or tissue from the individual. In a preferred embodiment, the test sample is a serum sample from an individual suspected of having multifocal motor neuropathy.

To determine the amount of anti-GM1 ganglioside antibody in a test sample, the GM1-coated, covalent-linkage solid-phase reactant is contacted with the test sample. A GM1-coated, covalent-linkage solid-phase reactant that has been contacted with a test sample is referred to herein as a "contacted GM1-coated, covalent-linkage solid-phase reactant." The contacted GM1-coated, covalent-linkage solid-phase reactant is maintained under appropriate conditions to allow binding of any antibody to GM1 ganglioside that may be present in the test sample to the GM1 ganglioside that is adsorbed onto the solid-phase reactant. The term, "antibody to GM1 ganglioside" (also referred to as "anti-GM1 ganglioside antibody") refers to an antibody or antibodies that binds to GM1 ganglioside in higher titers than to control antigens, such as glycolipids, glycoproteins or carbohydrates. A representative control antigen is GD1a ganglioside. The anti-GM1 ganglioside antibody may bind to GM1 ganglioside that is in a lipid environment (e.g., GM1 ganglioside in a lipid mixture of GM1 ganglioside, galactocerebroside, and cholesterol (GGC)), and/or may bind to GM1 ganglioside that is isolated (e.g., not in a lipid environment). The amount of anti-GM1 ganglioside IgM antibody in the test sample, if any, that has bound to the GM1 ganglioside on the covalent-linkage solid-phase reactant is determined.

The amount of antibody can be determined by a variety of methods using standard techniques, including enzyme-linked immunosorbent assay (ELISA), solid phase radioimmunoassay, or other solid phase immunoassays (see Ausubel, F. M. et al., eds., Current Protocols in Molecular Biology, John Wiley & Sons, 1996, especially units 11.2 (ELISA) and 11.16 (Determination of Specific Antibody Titer); the entire teachings of this reference are incorporated herein by reference). In a typical solid-phase immunoassay, the amount of antibody bound to the GM1 ganglioside adsorbed onto the covalent-linkage solid-phase reactant is determined using a developing reagent, such as a detection antibody that binds to the anti-GM1 ganglioside antibody. The detection antibody can be linked or conjugated to another molecule, such as an enzyme or fluorophore, to facilitate detection. Alternatively, the detection antibody is iodinated.

In a preferred embodiment, an ELISA assay is performed, using as a developing reagent a detection antibody that is linked to an enzyme, such as horseradish peroxidase. The contacted, solid phase-reactant is incubated with the developing reagent, forming a developed, contacted solid-phase reactant. Subsequently, a substrate of the enzyme is added to the developed, contacted solid-phase reactant, and the amount of activity of the enzyme on its substrate (e.g., the amount of hydrolysis of the substrate) is measured by an appropriate means, such as by measuring optical density.

Titers of anti-GM1 ganglioside antibodies can be calculated from the amount of detector antibody bound to the anti-GM1 ganglioside IgM autoantibody, using standard conversion algorithms. For example, if the developing reagent comprises horseradish peroxidase, titers of antibody can be calculated as set forth in Pestronk et al. (Ann. Neurol. 2.7:316–326 (1990)).

If a control antigen, such as GD1a ganglioside, is adsorbed on the covalent-linkage solid-phase reactant, titers of antibody binding to the control antigen are subtracted from the titers of antibody binding to GM1 ganglioside. The difference between the titer of antibody binding to GM1 ganglioside and the titer of antibody binding to the control antigen(s) is indicative of the selective binding of the antibody to GM1 ganglioside. If the control antigen is adsorbed on a separate covalent-linkage solid-phase reactant, the control antigen-coated, covalent-linkage solid-phase reactant is contacted with the test sample in the same manner as the GM1-coated, covalent-linkage solid-phase reactant and maintained under the same conditions. The amount of antibody to the control antigen is determined by the same method as is used to determine the amount of antibody to the GM1 ganglioside.

Multifocal motor neuropathy and immune-mediated motor neuropathy can be diagnosed using these methods of determining the amount of anti-GM1 ganglioside antibody. To diagnose these motor neuropathies, the test sample is a sample from an individual to be tested for the presence of multifocal motor neuropathy. The amount of anti-GM1 ganglioside IgM, IgG, and/or IgA antibody in the test sample is compared with the amount of comparable anti-GM1 ganglioside antibody in at least one comparable control sample (i.e., a sample of the same type(s) of antibody (IgM, IgG, and/or IgA) from an individual who is not afflicted by a motor neuropathy). The control sample can be a sample from any individual who is not afflicted with a motor neuropathy; it is not necessary that the control sample be from an individual who is free of disease. For example, the control sample can be a sample from an individual who has amyotrophic lateral sclerosis, systemic immune disorders, or idiopathic sensory-motor polyneuropathies. A "comparable" normal sample is a sample of the same type of body fluid or tissue as the test sample; alternatively, if the test sample is IgM antibodies isolated from a sample of fluid or tissue, the comparable normal or control sample is a sample of IgM antibodies isolated from the same type of bodily fluid or tissue. More than one control sample can be used. The presence of an amount of selective anti-GM1 ganglioside antibody binding in the test sample that is greater, by a titer of approximately 1,800, than the amount of selective anti-GM1 ganglioside antibody binding in a comparable control sample, correlates with a diagnosis of motor neuropathy.

The present invention also includes kits to be used in methods of the invention. Kits can include the following components: (1) a covalent-linkage solid-phase reactant having GM1 ganglioside adsorbed thereon (i.e., a GM1-coated, covalent-linkage solid-phase reactant); and (2) labeled detector antibody that binds to the anti-GM1 ganglioside autoantibody. The detector antibody can be specific for the type of antibody (e.g., IgM, IgG or IgA) Detector antibody can comprise an antibody bound to a detectable agent, such as an enzyme, radioactive molecule, or fluorescent agent. If the detector antibody is bound to an enzyme that reacts with an added substrate to yield a colored product, such as horseradish peroxidase, the kit can also include the substrate.

The invention is now further illustrated by the following Exemplification.

EXEMPLIFICATION

Comparison of Titers of Antibody to GM1 Ganglioside Using a Standard ELISA; to GM1 Ganglioside in a Lipid Mixture, Using a Standard ELISA; and to GM1 Ganglioside Using an ELISA with a Modified Solid-phase Reactant Serum samples. Serums from 27 patients with multifocal motor neuropathy (MMN) (Pestronk, A. et al., 1988, Ann. Neurol. 24:73–38; Kornberg, A. J. and Pestronk, A., 1995, Ann. Neurol. 37:S43–S50) were tested. As controls, 221 other serums were tested. These included 113 patients examined at the Neuromuscular Center at Washington University, St. Louis, Mo., USA, who met accepted criteria for diagnosis that included: chronic inflammatory demyelinating polyneuropathy (CIDP) (22 patients), demyelinating Guillain-Barré syndrome (GBS) (22 patients), amyotrophic lateral sclerosis (ALS) (clinically definite by World Federation of Neurology criteria) (22 patients), systemic immune disorders without neurologic involvement (22 patients), motor neuropathies (6 patients) and idiopathic sensory-motor polyneuropathies (19 patients). Serums were also evaluated from the following groups: patients with ALS included in a treatment trial of ciliary neurotrophic factor (67 patients), and Chinese patients with acute immune neuropathies (41 patients) (including subgroups with axonal (29 patients) and demyelinating (14 patients) findings on electrophysiological studies).

Antibody assays. Enzyme-linked immunosorbent assays were used to assay serums for IgM binding to purified glycolipids. Three different assays were used. In the first assay, conventional ELISA plates (Imulon) were used as previously described to detect antibodies to GM1 ganglioside (Pestronk, A. et al., 1994, Neurology 44:1131–1137; Pestronk, A. et al., 1990, Ann. Neurol. 27:316–326). For this assay, individual lipid antigens, including GM1 ganglioside (150 µg) and GD1a ganglioside (150 µg) (Sigma), in 50 µl of methanol were individually added to separate wells and evaporated to dryness.

In a second assay, conventional ELISA plates (Imulon) were used to detect antibodies to a lipid mixture, "GGC" (GM1 ganglioside (0.15 µg): galactocerebroside (1.5 µg): cholesterol (1.5 µg)). Individual lipids were dissolved in methanol, mixed in appropriate proportions, evaporated to dryness, reconstituted in phosphate-buffered saline (PBS) pH 7.2 (0.01 M with 0.15 M NaCl: 100 µl), placed in wells, incubated overnight at 4° C., and washed 3 times with 1% bovine serum albumin (BSA) in PBS (Pestronk, A. et al., 1997, Neurology 48:1104–1106).

In a third assay, modified ELISA plates were used to detect antibodies to GM1 ganglioside. Nunc CovaLink NH microwell plates (Nunc; Roskilde, Denmark), which are modified with secondary amino groups, were used. GM1 ganglioside (150 µg) and GD1a ganglioside (150 µg) were dissolved in 100 µl of 1% N-(3-dimethylaminopropyl)-N-ethyl-carbodimide (EDC) (Sigma), and incubated in wells overnight at 4° C. Plates were then washed three times with PBS-0.05% Tween 20. Using this procedure, glycolipids were covalently linked to the wells.

After overnight incubation and washing steps, each of the three assays was performed as follows: the remaining binding sites in all ELISA wells assays were blocked with 1% human serum albumin in PBS (100 µl) for 4 hours at room temperature. Plates were then washed 3 times with 1% bovine serum albumin (BSA) in PBS. Subsequent steps were performed at 4° C. Between steps, washing (×3) was performed using PBS with 1% BSA without detergent. All serums were tested in duplicate. Serum was tested by adding dilutions (1:10$^3$ to 1:10$^6$ in PBS with 1% BSA) to wells overnight. The binding of IgM was measured using 4 hour exposure to goat anti-human IgM linked to horseradish peroxidase (HRP) (Organon Teknika-Cappel; West Chester, Pa.) in PBS with 1% BSA (1:20,000). Color was developed with 100 μl substrate buffer (0.1 M citrate buffer, pH 4.5 with 0.004% H$_2$O$_2$ and 0.1% phenylenediamine) for 30 minutes. Optical density (OD) was determined at 450 nm. A serum antibody with a titer of x was detectable (>0.05 OD units over controls) up to a dilution of at least 1/x. The titer of selective serum IgM binding to GM1 ganglioside was then calculated by subtracting the level of serum IgM binding of GD1a. Based on initial control studies, titers of selective IgM anti-GM1 binding greater than 1,800 were deemed to be "high" titers. The results are shown in the Table, below.

TABLE

Binding of Serum IgM to GM1 Ganglioside and GGC

| Patient # | Titers of Serum, IgM vs. | | |
|---|---|---|---|
| | GM1, standard ELISA plate | GGC, standard ELISA plate | GM1, covalent-linkage plate |
| 1 | 0 | 9,500 | 1,200 |
| 2 | 0 | 35,000 | 31,000 |
| 3 | 900 | 4,400 | 29,000 |
| 4 | 1,900 | 3,600 | 42,000 |
| 5 | 110,000 | 6,500 | 370,000 |
| 6 | 53,000 | 7,200 | 180,000 |
| 7 | 10,000 | 6,000 | 61,000 |
| 8 | 0 | 0 | 5,800 |
| 9 | 0 | 0 | 2,600 |
| 10 | 0 | 0 | 2,200 |
| 11 | 0 | 0 | 4,600 |
| 12 | 0 | 0 | 2,600 |
| 13 | 10,000 | 8,000 | 13,000 |
| 14 | 0 | 0 | 3,400 |
| 15 | 1,200 | 600 | 1,900 |
| 16 | 2,600 | 3,400 | 10,000 |
| 17 | 0 | 1,900 | 3,700 |
| 18 | 0 | 0 | 0 |
| 19 | 0 | 0 | 0 |
| 20 | 0 | 5,000 | 12,000 |
| 21 | 1,000 | 1,200 | 22,000 |
| 22 | 0 | 0 | 3,400 |
| 23 | 0 | 0 | 1,900 |
| 24 | 0 | 0 | 2,100 |
| 25 | 2,500 | 4,000 | 10,000 |
| 26 | 0 | 0 | 5,400 |
| 27 | 0 | 0 | 13,300 |
| Mean ± S.E.M. | 7,152 ± 4,425 | 3,567 ± 1,338 | 30,815 ± 13,728 |

GGC = lipid mixture (GM1 ganglioside (0.15 μg), galactocerebroside (1.5 μg), cholesterol (1.5 μg)).
S.E.M. = standard error of the mean.
Results in patients 1 to 6 and 8 to 21 for IgM antibodies against GM1 ganglioside with standard plates, and for IgM antibodies against GGC, were reported previously (Pestronk, A. et al., 1997, Neurology 48:1104–1106).

The results showed that serums from 85% (23 of 27) MMN patients had high titers of selective IgM binding to GM1 ganglioside (greater than 1,800) when measured using the third assay methodology, with ELISA plates containing secondary amino groups (Table). This is significantly greater (p<0.001) than the percentages of the same MMN serums found to have selective IgM binding with testing against GM1 ganglioside (37%; 10 of 27)), or the GGC lipid mixture (52%; 14 of 27), on standard ELISA plates. Nine of the 27 serums had high IgM anti-GM1 ganglioside titers using the third assay methodology (range 1,900 to 13,300), but were negative using the other two types of assays. In addition to being detected more frequently with the amine-containing ELISA plates, the titers of IgM vs. GM1 in MMN patients were generally higher (p<0.001), averaging 30,815±14,728 compared to 7,152±4,425 with GM1 antibodies measured using standard plates and 3,567±1,338 with the GGC antigen.

Two other groups also frequently had high titers of selective IgM binding to GM1 ganglioside. Chinese patients with acute immune neuropathies had high titers (35%) of selective IgM binding. IgM anti-GM1 ganglioside titers were high in a similar proportion of the subgroups with predominantly axonal changes (11/29:38%) and with demyelination (29%:4/14). Titers in the group of Chinese patients with acute immune neuropathies were lower than those in MMN, averaging 2,123±516. Only 2% of serums (1 of 43) had a titer above 10,000 compared to 44% (12 of 27) of MMN patients (p<0.001). Two of 6 patients (33%) with chronic asymmetric motor neuropathies but no demyelination, had high titers of IgM binding to GM1 ganglioside(71,800). No serum from U.S. patients with GBS, CIDP, ALS, sensory-motor polyneuropathy, or systemic autoimmune disorders had high titers (>1,800) of selective IgM binding to GM1 ganglioside.

In a final experiment the effects of covalent binding of antigen to ELISA plates, on the measurement of another anti-glycolipid antibody, sulfatide, were measured. Covalent binding of sulfate to the covalent-linkage ELISA plates eliminated, rather than increased, specific IgM binding to that antigen. Serums with selective IgM anti-sulfatide titers of 5,400, 5,600, 7,800, and 2,800 detected using conventional ELISA plates showed no selective IgM binding to plates with sulfatide covalently linked to secondary amino groups.

Using covalently-bound GM1 ganglioside as antigen, the titers of IgM anti-GM1 antibodies in MMN were often quite high, averaging above 30,000 and with 12 of 27 patient serums above 10,000. MMN patients tested by standard ELISA methodology averaged 23% of the titers found using amino-linked GM1 ganglioside. The Chinese acute immune neuropathies, one of the two other groups with serums having titers of IgM vs. GM1 ganglioside above 1,800, averaged about 7% of the MMN level at 2,123±516. IgM anti-GM1 ganglioside antibodies were even present in Chinese patients (29%; 4 of 14) with demyelinating GBS-like disorders. This is in contrast (p=0.017) to the GBS patients in the U.S. in whom IgM anti-GM1 antibodies were not detected (0 of 22). This disparity suggests that GBS-like syndromes may have varying underlying immune pathogenesis, or at least predisposing events, in different geographic locations. IgM anti-GM1 antibodies were never found in serum samples from 44 patients with other demyelinating neuropathies, or in 80 serums from patients with another motor disorder, ALS, that is probably not immune-mediated.

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. An improved method of determining in a test sample the amount of antibody to GM1 ganglioside, in which the amount of antibody is determined by performing an assay using a solid phase reactant, wherein the improvement comprises using a solid-phase reactant modified to allow covalent linkage of compounds on its surface, thereby forming a covalent-linkage solid-phase reactant, the covalent-linkage solid-phase reactant having GM1 ganglioside covalently linked thereon.

2. The method of claim 1, wherein the covalent-linkage solid-phase reactant has secondary amino groups on its surface.

3. The method of claim 1, comprising performing an enzyme-linked immunosorbent assay to determine the amount of antibody to GM1 ganglioside.

4. A method of determining in a test sample the amount of antibody to GM1 ganglioside, comprising the steps of:
 a) providing a GM1-coated covalent-linkage solid-phase reactant, the GM1-coated covalent-linkage solid-phase reactant comprising a solid-phase reactant modified to allow covalent linkage of compounds on its surface, thereby forming a covalent-linkage solid-phase reactant, the covalent-linkage solid-phase reactant having GM1 ganglioside covalently linked thereon;
 b) contacting the GM1-coated covalent-linkage solid-phase reactant with a test sample, thereby forming a contacted GM1-coated covalent-linkage solid-phase reactant;
 c) maintaining the contacted GM1-coated covalent-linkage solid-phase reactant under appropriate conditions to allow antibody to GM1 ganglioside to bind to the GM1 ganglioside covalently linked on the covalent-linkage solid-phase reactant; and
 d) determining the amount of antibody to GM1 ganglioside that is bound to the GM1 ganglioside on the GM1-coated covalent-linkage solid-phase reactant.

5. The method of claim 4, wherein the covalent-linkage solid-phase reactant has secondary amino groups on its surface.

6. The method of claim 4, wherein the covalent-linkage solid-phase reactant additionally comprises at least one control antigen adsorbed on the covalent-linkage solid-phase reactant.

7. The method of claim 6, wherein the control antigen is selected from the group consisting of: a glycolipid, a glycoprotein, and a carbohydrate.

8. The method of claim 7, wherein the glycolipid is GD1a ganglioside.

9. The method of claim 4, wherein the solid-phase reactant is a microtiter plate.

10. The method of claim 4, wherein the amount of antibody to GM1 ganglioside that is bound to the GM1 ganglioside on the GM1-coated covalent-linkage solid-phase reactant is determined by incubating the contacted GM1-coated solid-phase reactant with a developing reagent.

11. The method of claim 10, wherein the developing reagent comprises a detection antibody that binds to antibody to GM1 ganglioside.

12. The method of claim 11, wherein the detection antibody is conjugated to an enzyme.

13. The method of claim 10, wherein the detection antibody is conjugated to a fluorophore.

14. The method of claim 10, wherein the detection antibody is iodinated.

15. A method of determining in a test sample the amount of antibody to GM1 ganglioside, comprising the step of:
 a) providing a GM1-coated covalent-linkage solid-phase reactant, the GM1-coated covalent-linkage solid-phase reactant comprising a solid-phase reactant modified to allow covalent linkage of compounds on its surface, thereby forming a covalent-linkage solid-phase reactant, the covalent-linkage solid-phase reactant having GM1 ganglioside covalently linked thereon;
 b) contacting the GM1-coated covalent-linkage solid-phase reactant with a test sample, thereby forming a contacted GM1-coated covalent linkage solid-phase reactant;
 c) maintaining the contacted GM1-coated covalent-linkage solid-phase reactant under conditions that allow antibody to GM1 ganglioside, if present in the test sample, to bind to the GM1 ganglioside covalently linked on the covalent-linkage solid-phase reactant;
 d) incubating the contacted GM1-coated covalent-linkage solid-phase reactant with a detection antibody that bind to the antibody to GM1 ganglioside, wherein the detection antibody is conjugated to an enzyme, thereby forming a developed, contacted GM1-coated covalent-linkage solid-phase reactant;
 e) adding a substrate of the enzyme to the developed, contacted GM1-coated covalent-linkage solid-phase reactant; and
 f) measuring the amount of activity of the enzyme,
wherein the amount of antibody to GM1 ganglioside is proportional to the amount of activity of the enzyme.

16. A method of diagnosing a motor neuropathy in an individual, comprising determining the titer of antibody to GM1 ganglioside in a test sample from the individual by conducting an assay using a covalent-linkage solid-phase reactant modified to allow covalent linkage of compounds on its surface, thereby forming a covalent-linkage solid-phase reactant, the covalent-linkage solid-phase reactant having GM1 ganglioside covalently linked thereon, wherein a titer greater than approximately 1,800 is indicative of motor neuropathy.

17. The method of claim 16, wherein the motor neuropathy is multifocal motor neuropathy.

18. The method of claim 16, wherein the motor neuropathy is immune-mediated motor neuropathy.

19. The method of claim 16, comprising conducting an enzyme-linked immunosorbent assay to determine the amount of antibody to GM1 ganglioside.

20. A method of diagnosing a motor neuropathy in an individual, comprising the steps of:
 a) providing a GM1-coated covalent-linkage solid phase reactant, the GM1-coated covalent-linkage solid-phase reactant comprising a solid-phase reactant modified to allow covalent linkage of compounds on its surface, thereby forming a covalent-linkage solid-phase reactant, the covalent-linkage solid-phase reactant having GM1 ganglioside covalently linked thereon;
 b) contacting the GM1-coated covalent-linkage solid-phase reactant with a test sample from the individual, thereby forming a contacted GM1-coated covalent-linkage solid-phase reactant;
 c) maintaining the contacted GM1-coated covalent-linkage solid-phase reactant under appropriate conditions to allow antibody to GM1 ganglioside, if present in the test sample, to bind to the GM1 ganglioside covalently linked on the GM1-coated covalent-linkage solid-phase reactant; and
 d) determining the titer of antibody to GM1 ganglioside bound to GM1 ganglioside on the GM1-coated covalent-linkage solid-phase reactant,
wherein a titer of antibody to GM1 ganglioside that is greater than approximately 1,800 is indicative of a motor neuropathy.

21. The method of claim 20, wherein the motor neuropathy is multifocal motor neuropathy.

22. The method of claim 20, wherein the motor neuropathy is immune-mediated motor neuropathy.

23. The method of claim 20, wherein the solid-phase reactant is a microtiter plate.

24. The method of claim 20, wherein the test sample is selected from the group consisting of: blood, serum, cerebrospinal fluid and urine.

25. A method of diagnosing a motor neuropathy in an individual, comprising the step of:
   a) providing a GM1-coated covalent-linkage solid-phase reactant, the GM1-coated covalent-linkage solid-phase reactant comprising a solid-phase reactant modified to allow covalent linkage of compounds on its surface, thereby forming a covalent-linkage solid-phase reactant, the covalent-linkage solid-phase reactant having GM1 ganglioside covalently linked thereon and a control antigen covalently linked thereon;
   b) contacting the GM1-coated covalent-linkage solid-phase reactant with a test sample, thereby forming a contacted, GM1-coated covalent-linkage solid-phase reactant;
   c) maintaining the contacted, GM1-coated covalent-linkage solid-phase reactant under appropriate conditions to allow antibody to GM1 ganglioside, if present in the test sample, to bind to the GM1 ganglioside covalently linked on the covalent-linkage solid-phase reactant, and antibody to the control antigen, if present in the test sample, to bind to the control antigen covalently linked on the covalent-linkage solid-phase reactant;
   d) determining the titer of antibody to GM1 ganglioside that is bound to the GM1 ganglioside on the covalent-linkage solid-phase reactant;
   e) determining the titer or antibody to the control antigen that is bound to the control antigen on the covalent-linkage solid-phase reactant; and
   f) subtracting the titer of antibody to the control antigen from the titer of antibody to GM1 ganglioside,
      wherein a difference that is greater than approximately 1,800 is indicative of a motor neuropathy.

26. The method of claim 25, wherein the motor neuropathy is multifocal motor neuropathy.

27. The method of claim 25, wherein the motor neuropathy is immune-mediated motor neuropathy.

28. The method of claim 25, wherein the solid-phase reactant is a microtiter plate.

29. The method of claim 25, wherein the test sample is selected from the group consisting of: blood, serum, cerebrospinal fluid and urine.

30. A kit for detecting the amount of antibody to GM1 ganglioside in a sample, comprising a solid-phase reactant modified to allow covalent linkage of compounds on its surface, the solid-phase reactant having GM1 ganglioside covalently linked thereon.

31. The kit of claim 30, wherein the solid-phase reactant is a microtiter plate.

* * * * *